United States Patent [19]

Listemann et al.

[11] Patent Number: 5,136,094
[45] Date of Patent: Aug. 4, 1992

[54] PROCESS FOR THE SYNTHESIS OF SECONDARY FORMAMIDES

[75] Inventors: Mark L. Listemann, Whitehall; Ronald Pierantozzi, Orefield; Robert K. Pinschmidt, Jr., Allentown, all of Pa.

[73] Assignee: Air Products and Chemicals, Inc., Allentown, Pa.

[21] Appl. No.: 166,287

[22] Filed: Mar. 10, 1988

[51] Int. Cl.$^5$ .................. C07C 231/12; C07C 233/18
[52] U.S. Cl. ..................................... 564/244; 564/185
[58] Field of Search ................ 564/185, 186, 219, 224

[56] References Cited

U.S. PATENT DOCUMENTS

| | | | |
|---|---|---|---|
| 4,018,826 | 4/1977 | Gless, Jr. et al. | 260/583 P |
| 4,322,271 | 3/1982 | Jensen et al. | 204/73 R |
| 4,334,097 | 6/1982 | Schmidt | 564/201 |
| 4,554,377 | 11/1985 | Stackman et al. | 564/205 |
| 4,567,300 | 1/1986 | Murao et al. | 564/215 |

FOREIGN PATENT DOCUMENTS 1273533  7/1968  Fed. Rep. of Germany.

OTHER PUBLICATIONS

Robert W. Stackman, Richard H. Summerville, "Synthesis of N-Vinylacetamide and Preparation of Some Polymers and Copolymers", Ind. Eng. Chem. Prod. Res. Dev., 1985, 24, pp. 242-246.

*Primary Examiner*—Carolyn Elmore
*Attorney, Agent, or Firm*—Russell L. Brewer; James C. Simmons; William F. Marsh

[57] ABSTRACT

Secondary formamides having the structural formula:

$$R^1CHR^2CH(OR^3)NHCHO$$

wherein
 $R^1$ is H, $C_1$–$C_6$ alkyl or aryl;
 $R^2$ is H, or $C_1$–$C_6$ alkyl; and
 $R^3$ is benzyl, $C_1$–$C_8$ alkyl or hydroxyalkyl;

are synthesized by reacting an acetal having the structural formula: $R^1CHR^2CH(OR^3)_2$ wherein $R^1$, $R^2$ and $R^3$ are as defined above, with formamide in the presence of a strong acid catalyst at a temperature in the range of 0°–200° C.

16 Claims, No Drawings

PROCESS FOR THE SYNTHESIS OF SECONDARY FORMAMIDES

TECHNICAL FIELD OF THE INVENTION

The present invention relates to the synthesis of various secondary formamide compounds.

BACKGROUND OF THE INVENTION

Secondary N-vinyl carboxylic acid amides can be polymerized to give water-soluble homopolymers and copolymers. Such polymerizations are disclosed in Gless, et al., U.S. Pat. No. 4,018,826. The N-vinyl carboxylic acid amides used in the polymerization can be obtained by removing an alcohol from N-(1-alkoxyethyl)carboxylic acid amides. Jensen, et al., U.S. Pat. No. 4,322,271 discloses a three-stage process for forming N-vinyl-N-alkyl-carboxylic acid amides starting from N-ethyl-carboxylic acid amides. The N-ethyl-carboxylic acid amides undergo anodic alkoxylation to form N-$\alpha$-alkoxyethyl-carboxylic acid amides which are subsequently heated to split off an alcohol and form the final product. Stockman, et al. U.S. Pat. No. 4,554,377 discloses a process for preparing N-$\alpha$-alkoxyethyl-carboxylic acid amides from dimethyl acetal and a carboxylic acid amide, and subsequently for the synthesis of secondary N-vinyl carboxylic acid amides therefrom.

While the above-described methods have been applied for forming secondary N-vinyl carboxylic acid amides, existing methods for the preparation of the starting materials; i.e., N-(1-alkoxyethyl) carboxylic acid amides are inefficient and impractical when applied on an industrial scale. Such methods for forming N-(1-alkoxyethyl) carboxylic acid amides include the electrochemical alkoxylation of N-ethyl carboxylic acid amides with alcohols. While the electrochemical processes do operate cleanly and in good yields, the operations are complex and recovery of the conducting salts is expensive.

Schmidt, U.S. Pat. No. 4,334,097 discloses a process for preparing N-$\alpha$-alkoxylalkyl-carboxamides by reacting primary or secondary amides of aliphatic, araliphatic or aromatic carboxylic acids or cyclic carboxamides which are not capable of forming an aromatic system, with open-chain $\alpha$ halogenoalkyl ethers in the presence of tertiary amines. This process, however, requires the disposal of large quantities of acid salts.

Primary alkyl carboxylic acid amides react with acetaldehyde dimethyl acetal to give N-(1-methoxyethyl) carboxylic acid amides. This process requires large excesses of acetal; i.e., about 20:1; to achieve practical yields and purities, and is reported to fail for formamide. See R. W. Stackman, et al., *Ind. Eng. Chem. Prod. Res. Dev.* (1985), 24, 242–246.

Murao, et al., U.S. Pat. No. 4,567,300 and Great Britain equivalent 2 152 929 A discloses a process wherein acetaldehyde reacts with formamide in the presence of a weakly basic catalyst to yield solid N-(1-hydroxyethyl) formamide which, following catalyst neutralization, reacts with alcohols in the presence of an acid catalyst to yield N-(1-alkoxyethyl) formamide. This process is unattractive in that it requires two discrete steps, the handling of a solid intermediate, and the disposal of salts.

H. Bestian, et al., German Patent 1,273,533, discloses the synthesis of tertiary N-(1-alkoxyethyl) carboxylic acid amides from the reaction of acetaldehyde, alcohol, and secondary amide at 50°–150° C. using a 1.5–4 molar excess of acetaldehyde vs. amide.

BRIEF SUMMARY OF THE INVENTION

The present invention is a process for synthesizing secondary formamides having the structural formula:

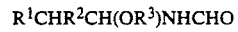

wherein:
R$^1$ is H, C$_1$–C$_6$ alkyl or aryl;
R$^2$ is H, or C$_1$–C$_6$ alkyl; and
R$^3$ is benzyl, C$_1$–C$_8$ alkyl or hydroxyalkyl; The process comprises reacting an acetal having the structural formula: R$^1$CHR$^2$CH(OR$^3$)$_2$ wherein R$^1$, R$^2$ and R$^3$ are as defined above, with formamide in the presence of a strong acid catalyst at a temperature in the range of 0°–200° C.

Contrary to prior art teachings, it has now been found that the above-described acetals will react with formamide in the presence of a strong acid catalyst to produce high yields of secondary formamide product having the above structural formula.

DETAILED DESCRIPTION OF THE INVENTION

Secondary formamides having the structural formula:

wherein:
R$^1$ is H, C$_1$–C$_6$ alkyl or aryl; R$^2$ is H, or C$_1$–C$_6$ alkyl; and R$^3$ is benzyl, C$_1$–C$_8$ alkyl or hydroxyalkyl are synthesized by the reaction of an acetal with formamide in the presence of a strong acid catalyst. Acetals suitable for this reaction are any which have the structural formula R$^1$CHR$^2$CH(OR$^3$)$_2$ wherein R$^1$, R$^2$ and R$^3$ are as defined above.

The reaction is carried out in the presence of a strong acid catalyst, of which preferred examples include the macroreticular anhydrous sulfonic acid resin Amberlyst 15 and XN-1010 both available commercially from Rohm & Haas, and CH$_3$SO$_3$H. Generally, the strong acid catalyst should be present in a concentration of at least 0.1 mole % compared to formamide, with preferred ranges typically being significantly higher and depending upon the particular catalyst and acetal used. For example, when using XN-1010 resin, the optimum loading is 22–26 mole % H$^+$ based on formamide when using CH$_3$CH(OCH$_3$)$_2$. whereas for the same catalyst the optimum loading is 16–20 mole % H$^+$ when using CH$_3$CH(OCH$_2$CH$_3$)$_2$.

It has been found that the acid catalyzed reaction of acetal and formamide to form the above-described product proceeds as follows:

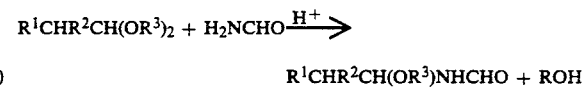

and can be carried out without handling solids and without forming salts.

For best results, the reactants should be added in an acetal:formamide molar ratio of at least 1:1 and preferably between 2:1 to 6:1. The reaction is run at a temperature from about 0°–200° C. with a preferred range typically being about 60°–100° C. for a time ranging from about 0.25-24 h, and preferably from 2-4 h, and typically at atmospheric or autogeneous pressure.

The reaction is best run undiluted, as the presence of a solvent, while not detrimental to selectivities, in some cases tends to lower conversions. If a solvent is used, it should be one capable of forming a single acetal/formamide/solvent liquid phase, examples of which include THF, dioxane, N-methylpyrrolidinone and the like. Small amounts of water may increase product yields and hence it is preferred to have between 0.1-2 mole equivalents of water based on formamide. More than 2 mole eq., however, may be detrimental to the system. Additionally, hydrated strong acid resins are generally less effective catalysts for the reaction than anhydrous resins.

The following examples were carried out to further illustrate the present invention and are not meant to be limiting.

EXAMPLE 1

Several runs were carried out in accordance with the process of the present invention to produce secondary formamides by reacting various acetals with formamide in a molar ratio of about 2:1 respectively. The reactions were catalyzed by various strong acid catalysts at several concentrations. The reactions were run, undiluted, at about 80° C. after which the products were collected and analyzed. The catalyst types and concentrations, reactants and run times, along with the product yields are reported in Table 1 below.

TABLE 1

Acetaldehyde Dialkyl Acetal
$2\ CH_3CH(OR)_2 + H_2NCHO \rightarrow CH_3CH(OR)NHCHO$

| R | Catalyst (mole eq.)[a] | Temp. (°C.) | Time (h) | % Yields[b] $CH_3CH(OR)NHCHO$ | $CH_3CH(NHCHO)_2$ |
|---|---|---|---|---|---|
| Me | XN-1010(0.18) | 80 | 1 | 37 | 6 |
| " | " | " | 2 | 41 | 7 |
| " | " | " | 3 | 39 | 7 |
| Me | $H_2SO_4$(0.06) | 80 | 1 | 24 | 7 |
| " | " | " | 2 | 26 | 8 |
| " | " | " | 3 | 26 | 7 |
| Me | $CH_3SO_3H$(0.06) | 80 | 1 | 18 | 3 |
| " | " | " | 2 | 18 | 3 |
| Et | XN-1010(0.18) | 80 | 1 | 54 | 20 |
| " | " | " | 2 | 58 | 20 |
| " | " | " | 3 | 58 | 21 |
| Et | $H_2SO_4$(0.06) | 80 | 1 | 43 | 18 |
| " | " | " | 2 | 43 | 19 |
| " | " | " | 3 | 44 | 19 |
| Et | $CH_3SO_3H$(0.06) | 80 | 1 | 51 | 15 |
| " | " | " | 2 | 50 | 14 |
| Pr | XN-1010(0.18) | 80 | 1 | 27 | 11 |
| " | " | " | 2 | 30 | 14 |
| Pr | $H_2SO_4$(0.06) | 80 | 1 | 37 | 12 |
| " | " | " | 2 | 39 | 11 |
| Pr | $CH_3SO_3H$(0.06) | 80 | 1 | 36 | 12 |
| " | " | " | 2 | 35 | 12 |

[a]Catalyst mole equivalents relative to formamide.
[b]All yields based on formamide.

The present process is advantageous over the prior art methods, such as Murao, U.S. Pat. No. 4,567,300, in that it is operated in a single step, free of solids handling and salt disposal. Additionally, contrary to the teachings of R. H. Summerville, et al. *Polymer Preprints* (1983) 24, 12-13, it has now been demonstrated that formamide can be used in this type of process to yield the desired products. The process affords high formamide conversions with good product selectivity, and requires minimum reactant recycle. With preferred catalysts, no salts are generated and catalyst separation is straightforward.

From the results reported in Table 1 above, it can be seen that all three acid catalysts resulted in good product ($CH_3CH(OR)NHCHO$) yield with low byproducts; $CH_3CH(NHCHO)_2$. Product yield was highest for the runs using Acetaldehyde Diethyl Acetal, although byproduct yield also increased. Reaction time ranging from 1-3h had little effect on product yield.

EXAMPLE 2

Several runs were carried out to determine the effect of temperature on the reaction of the present invention when using either Acetaldehyde Diethyl Acetal or Acetaldehyde Dimethyl Acetal as a reactant with formamide. The process conditions and results of these runs are set out in Table 2 below.

TABLE 2

Effect of Reaction Temperature
$2\ CH_3CH(OR)_2 + H_2NCHO \rightarrow CH_3CH(OR)NHCHO$

| R | Catalyst (mole eq.)[a] | Temp. (°C.) | Time (h) | % Yields[b] $CH_3CH(OR)NHCHO$ | $CH_3CH(NHCHO)_2$ |
|---|---|---|---|---|---|
| Me | XN-1010(0.18) | 60 | 1 | 36 | 4 |
| " | " | " | 2 | 41 | 4 |
| Me | XN-1010(0.18) | 80 | 1 | 37 | 6 |
| " | " | " | 2 | 41 | 7 |
| " | " | " | 3 | 39 | 7 |
| Me | XN-1010(0.18) | 100 | 1 | 39 | 7 |
| " | " | " | 2 | 43 | 8 |

TABLE 2-continued

Effect of Reaction Temperature
$2\ CH_3CH(OR)_2 + H_2NCHO \rightarrow CH_3CH(OR)NHCHO$

| R | Catalyst (mole eq.)[a] | Temp. (°C.) | Time (h) | % Yields[b] CH$_3$CH(OR)NHCHO | CH$_3$CH(NHCHO)$_2$ |
|---|---|---|---|---|---|
| " | " | " | 3 | 45 | 9 |
| Et | XN-1010(0.18) | 60 | 1 | 62 | 9 |
| " | " | " | 2 | 67 | 10 |
| " | " | " | 3 | 68 | 10 |
| Et | XN-1010(0.18) | 80 | 1 | 54 | 20 |
| " | " | " | 2 | 58 | 20 |
| " | " | " | 3 | 58 | 21 |
| Et | XN-1010(0.18) | 100 | 1 | 48 | 21 |
| " | " | " | 2 | 57 | 28 |
| " | " | " | 3 | 57 | 27 |

[a]Catalyst mole equivalents relative to formamide.
[b]All yields based on formamide.

The results reported above show that good yields of secondary formamide product was obtained for all of the runs, indicating that the process of the present invention can be run at a wide range of temperatures. As temperature increased, however, the amount of unwanted byproduct (Bis) also increased.

EXAMPLE 3

Several runs were carried out to determine the effect various acetal:formamide ratios have on product distribution when using Acetaldehyde Dimethyl Acetal as the reactant. The runs were carried out at 80° C. over a strong acid catalyst (0.24 mole eq. XN-1010). The specific ratios, along with the product yields, are set out in Table 3 below.

TABLE 3

Acetaldehyde Dimethyl Acetal:Formamide Ratio
$X\ CH_3CH(OMe)_2 + H_2NCHO \rightarrow CH_3CH(OMe)NHCHO$

| Acetal:Amide Ratio | Catalyst (mole eq.)[a] | Temp. (°C.) | Time (h) | % Yields[b] CH$_3$CH(OMe)NHCHO | CH$_3$CH(NHCHO)$_2$ |
|---|---|---|---|---|---|
| 2:1 | XN-1010(0.24) | 80 | 1 | 53 | 7 |
| " | " | " | 2 | 51 | 7 |
| " | " | " | 3 | 53 | 8 |
| 4:1 | XN-1010(0.24) | 80 | 1 | 54 | 7 |
| " | " | " | 2 | 57 | 6 |
| 6:1 | XN-1010(0.24) | 80 | 1 | 56 | 4 |
| " | " | " | 2 | 55 | 4 |
| 20:1 | XN-1010(0.24) | 80 | 1 | 58 | 0 |
| " | " | " | 2 | 63 | 0 |

[a]Catalyst mole equivalents based on formamide.
[b]% yields based on formamide.

As can be seen from the results reported above, acetal:amide ratios ranging from 2:1 to 20:1 all produced high yields of desired product. Increasing the ratio from 6:1 to 20:1, however, only showed a slight increase in product yield, and slight decrease in the yield of Bis.

EXAMPLE 4

Several runs were also carried out to determine the effect various acetal:formamide ratios have on product distribution when using Acetaldehyde Diethyl Acetal as the reactant. The reaction conditions, reactant ratios and product yields for these runs are set out in Table 4 below.

TABLE 4

Acetaldehyde Diethyl Acetal:Formamide Ratio
$X\ CH_3CH(OEt)_2 + H_2NCHO \rightarrow CH_3CH(OEt)NHCHO$

| Acetal:Amide Ratio | Catalyst (mole eq.)[a] | Temp. (°C.) | Time (h) | % Yields[b] CH$_3$CH(OEt)NHCHO | CH$_3$CH(NHCHO)$_2$ |
|---|---|---|---|---|---|
| 2:1 | XN-1010(0.18) | 60 | 1 | 62 | 9 |
| " | " | " | 2 | 67 | 10 |
| " | " | " | 3 | 68 | 10 |
| 4:1 | XN-1010(0.18) | 60 | 1 | 57 | 9 |
| " | " | " | 2 | 65 | 10 |
| " | " | " | 3 | 68 | 10 |
| 6:1 | XN-1010(0.18) | 60 | 1 | 65 | 0 |
| " | " | " | 2 | 70 | 0 |
| " | " | " | 3 | 72 | 0 |
| 20:1 | XN-1010(0.18) | 60 | 1 | 69 | 0 |
| " | " | " | 2 | 78 | 0 |
| " | " | " | 3 | 82 | 0 |
| 2:1 | XN-1010(0.18) | 80 | 1 | 54 | 20 |
| " | " | " | 2 | 58 | 20 |
| 4:1 | XN-1010(0.18) | 80 | 1 | 62 | 13 |
| " | " | " | 2 | 68 | 6 |
| 6:1 | XN-1010(0.18) | 80 | 1 | 61 | 9 |
| " | " | " | 2 | 64 | 9 |

TABLE 4-continued

Acetaldehyde Diethyl Acetal:Formamide Ratio
$\times$ CH$_3$CH(OEt)$_2$ + H$_2$NCHO $\rightarrow$ CH$_3$CH(OEt)NHCHO

| Acetal:Amide Ratio | Catalyst (mole eq.)[a] | Temp. (°C.) | Time (h) | % Yields[b] CH$_3$CH(OEt)NHCHO | CH$_3$CH(NHCHO)$_2$ |
|---|---|---|---|---|---|
| 20:1 | XN-1010(0.18) | 80 | 1 | 21 | 0 |
| " | " | " | 2 | 22 | 0 |

[a] Mole equivalents of catalyst relative to formamide.
[b] % yields based on formamide.

The results reported in Table 4 indicate that acetal:-formamide ratios ranging from 2:1 to 20:1 all produced good yields of desired product, with the exception of the run wherein a ratio of 20:1 was used at a temperature of 80° C. Good results were obtained for the same reactant ratio when run at 60° C. however.

EXAMPLE 5

Several runs were carried out in accordance with the present invention to compare the effect of running the reaction in batch with running it with semi-continuous addition of acid catalyst. The reaction conditions, including catalyst loading, along with the product yields are set out in Table 5 below.

TABLE 5

Batch vs. Semi-Continuous Addition of Acid
2 CH$_3$CH(OR)$_2$ + H$_2$NCHO $\rightarrow$ CH$_3$CH(OR)NHCHO

| R | Catalyst (mole eq.)[a] | Temp. (°C.) | Time (h) | % Yields[b] CH$_3$CH(OR)NHCHO | CH$_3$CH(NHCHO)$_2$ |
|---|---|---|---|---|---|
| Me | XN-1010(0.18) | 80 | 1 | 37 | 6 |
| " | " | " | 2 | 41 | 7 |
| " | " | " | 3 | 39 | 7 |
| Me | XN-1010(0.06) | 80 | 1 | 16 | 5 |
| " | Further 0.06 | " | 2 | 25 | 7 |
| " | " | " | 3 | 36 | 9 |
| Me | H$_2$SO$_4$(0.06) | 80 | 1 | 24 | 7 |
| " | " | " | 2 | 26 | 8 |
| " | " | " | 3 | 26 | 7 |
| Me | H$_2$SO$_4$(0.02) | 80 | 1 | 15 | 3 |
| " | Further 0.02 | " | 2 | 22 | 5 |
| " | " | " | 3 | 26 | 6 |
| Et | XN-1010(0.18) | 80 | 1 | 54 | 20 |
| " | " | " | 2 | 58 | 20 |
| " | " | " | 3 | 58 | 21 |
| Et | XN-1010(0.06) | 80 | 1 | 16 | 11 |
| " | Further 0.06 | " | 2 | 31 | 18 |
| " | " | " | 3 | 47 | 19 |
| Et | H$_2$SO$_4$(0.06) | 80 | 1 | 43 | 18 |
| " | " | " | 2 | 43 | 19 |
| " | " | " | 3 | 44 | 19 |
| Et | H$_2$SO$_4$(0.02) | 80 | 1 | 30 | 5 |
| " | Further 0.02 | " | 2 | 34 | 6 |
| " | " | " | 3 | 44 | 8 |

[a] Mole equivalents of catalyst relative to formamide.
[b] % yields based on formamide.

The results reported in Table 5 above for these runs indicate that there is not an appreciable difference in final product yield (i.e., total yield after 3h) between the runs carried out in batch and the runs with semi-continuous addition of catalyst. Operating the system in batch, however, achieves high product yields faster.

What is claimed is:

1. A process for the synthesis of secondary formamides having the structural formula:

R$^1$CHR$^2$CH(OR$^3$)NHCHO wherein:
R$^1$ is H, C$_1$-C$_6$ alkyl or aryl;
R$^2$ is H, or C$_1$-C$_6$ alkyl; and
R$^3$ is benzyl, C$_1$-C$_8$ alkyl or hydroxyalkyl; and said process comprising reacting an acetal having the structural formula: R$^1$CHR$^2$CH(OR$^3$)$_2$ wherein R$^1$, R$^2$ and R$^3$ are as defined above, with formamide, having the structural formula H$_2$NCHO, in the presence of a strong acid catalyst present in a concentration of at least 6 mole % of H$^+$ compared to formamide, at a temperature in the range of 0°-200° C.

2. A process in accordance with claim 1 wherein said reaction is carried out at autogeneous pressure.

3. A process in accordance with claim 1 wherein said temperature range is from 60°-100° C.

4. A process in accordance with claim 1 wherein said reaction is carried out for a period of time from 0.25 to 24 hours.

5. A process in accordance with claim 4 wherein said reaction is carried out for a period of time from 2 to 4 hours.

6. A process in accordance with claim 1 wherein the strong acid catalyst is macroreticular anhydrous sulfonic acid resin.

7. A process in accordance with claim 1 wherein the reactants are added in an acetal:formamide ratio of at least 1:1.

8. A process in accordance with claim 7 wherein the reactants are added in an acetal:formamide ratio in a range of 2:1 to 6:1.

9. A process in accordance with claim 1 wherein Acetaldehyde Diethyl Acetal and formamide are reacted to form N-(1-ethoxyethyl)-formamide.

10. A process in accordance with claim 9 wherein said strong acid catalyst is present in a concentration of 16-20 mole % of H+ compared to formamide.

11. A process in accordance with claim 1 wherein Acetaldehyde Dimethyl Acetal and formamide are reacted to form N-(1-methoxyethyl) formamide.

12. A process in accordance with claim 11 wherein said strong acid catalyst is present in a concentration of 22-26 mole % of H+ compared to formamide.

13. A process in accordance with claim 1 wherein said reaction is carried out at atmospheric pressure.

14. A process in accordance with claim 1 wherein said acetal is added in a concentration such that the acetal:formamide ratio is at least 1:1.

15. A process in accordance with claim 1 wherein the reaction is run in the presence of water.

16. A process in accordance with claim 15 wherein water is present in a concentration between 0.1-2 mole eq. based on formamide.

* * * * *